United States Patent [19]
Thompson

[11] Patent Number: 5,156,622
[45] Date of Patent: * Oct. 20, 1992

[54] APPARATUS AND PROCESS FOR APPLICATION AND ADJUSTABLE REPROFILING OF SYNTHETIC LENTICULES FOR VISION CORRECTION

[76] Inventor: Keith P. Thompson, 4584 E. Brookhaven Dr., Atlanta, Ga. 30319

[*] Notice: The portion of the term of this patent subsequent to May 8, 2007 has been disclaimed.

[21] Appl. No.: 371,538

[22] Filed: Jun. 26, 1989

Related U.S. Application Data

[63] Continuation-in-part of Ser. No. 163,519, Mar. 2, 1988, Pat. No. 4,923,467.

[51] Int. Cl.⁵ ................................................. A61F 2/14
[52] U.S. Cl. ............................................. 623/5; 623/4
[58] Field of Search ........................................ 623/4, 5

[56] References Cited

U.S. PATENT DOCUMENTS 4,923,467 5/1990 Thompson .............................. 623/5

Primary Examiner—Richard J. Apley
Assistant Examiner—D. F. Crosby
Attorney, Agent, or Firm—Hopkins & Thomas

[57] ABSTRACT

An apparatus and process for applying a synthetic lenticule to the cornea of a human eye is disclosed, the process also contemplating selective reprofiling of the lenticule while it is in place over the cornea. The process involves securing the lenticule over the cornea with an adhesive, thus leaving the visual axis of the eye undisturbed. The lenticule is placed over the cornea with a unique micromanipulation apparatus. A laser delivery system is used to reprofile the lenticule if necessary for refining the refractive power of the lenticule.

28 Claims, 5 Drawing Sheets

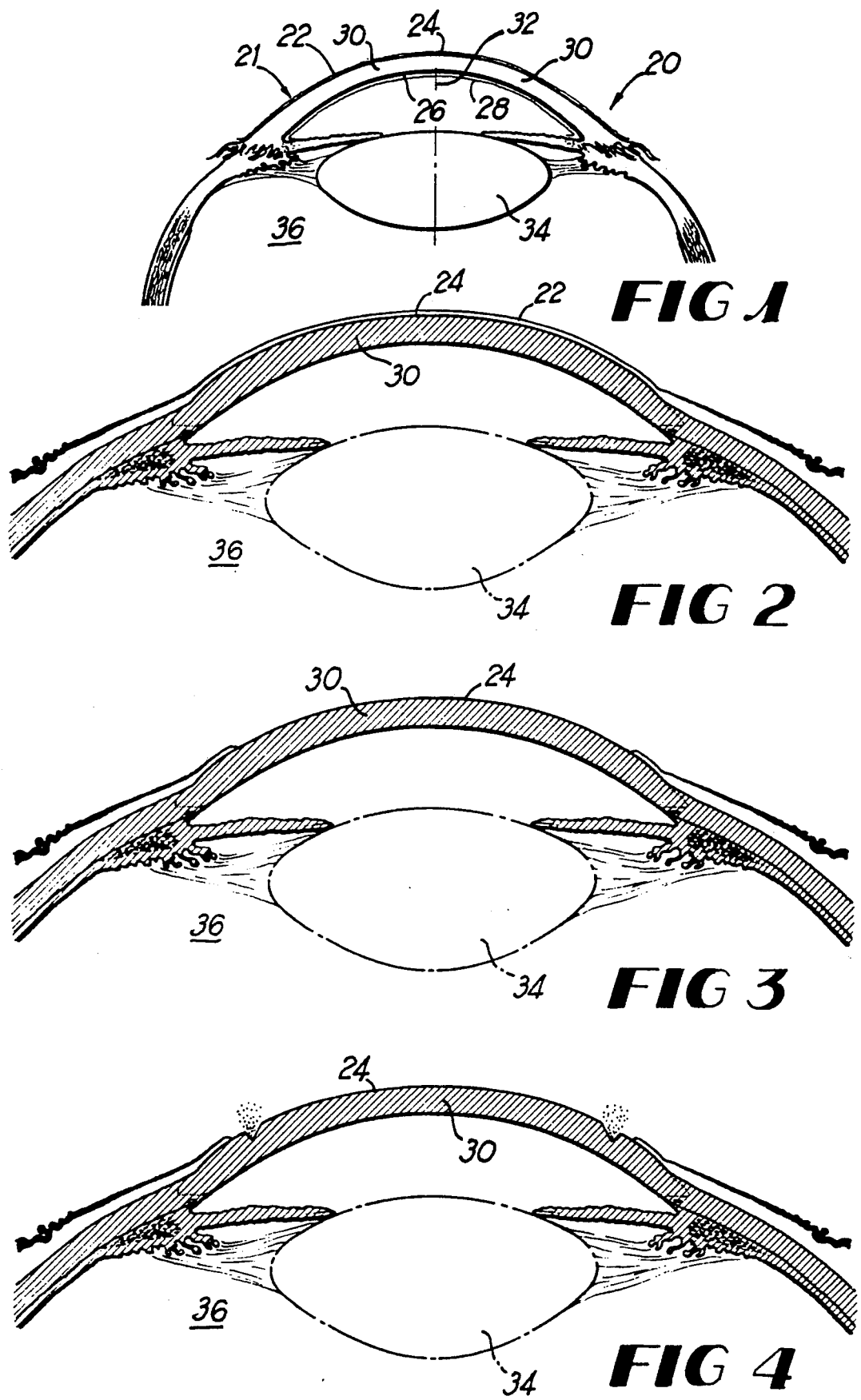

APPARATUS AND PROCESS FOR APPLICATION AND ADJUSTABLE REPROFILING OF SYNTHETIC LENTICULES FOR VISION CORRECTION

This application is a continuation-in-part of co-pending application Ser. No. 07/163,519 filed Mar. 2, 1988, now U.S. Pat. No. 4,923,467.

BACKGROUND OF THE INVENTION

Thirty to forty percent of the human population develop an ocular refractive error requiring correction by glasses, contact lens, or surgical means. Refractive errors result when the optical elements of the eye, the cornea and the lens, fail to image light directly on the retina. If the image is focused in front of the retina, myopia (nearsightedness) exists. An eye which focuses images behind the retina is said to hyperopic (fairsighted). An eye which has power that varies significantly in different meridians is said to be astigmatic. The focusing power of the eye is measured in units called diopters. The cornea is responsibel for about two-thirds of the eye's 60 diopter refracting power. The crystalline lens contributes the remainder.

The search to find a permanent cure of refractive erros, including myopia, hyperopic, or astigmatism has gone on for many years. An effective, safe, predictable, and stable correction for these ametropias would have enormous social and economic impact.

Ophthalmologists have derived a number of surgical procedures which attempt to correct refractive errors. None of these techniques have gained widespread acceptance because of procedures generally have unpredictable outcomes and undesirable side effects such as glare, fluctuating vision, and corneal scarring. Unpredictable refractive outcome is the primary reason radial keratotomy has not been accepted by a majority of ophthalmologists as an effective treatment for myopia. Two other recent techniques to correct ametropias are briefly described below.

Epikeratophakia (meaning lens on top of the cornea) is a technique in which a portion of a donor corena is used to make a lens which is sewn or glued to the surface of the patient's cornea in an attempt to correct his refractive error. This procedure involves freezing the donor corneal tissue and grinidn ghe posterior surface to achieve the desired optical configuration. This donor lenticule is then usually sewn into a groove in the patient's cornea cut by a circular mechanical trephine with hand dissection of a circular pocket. Epikeratophakia is used primarily in patients who have had cataract operations and in whom an intraocular lens is contraindicated, such as children or older patients with certain eye diseases, and has also been used to correct for myopia.

There are several problems with epikeratophakia which render its routine use for patients with refractive errors unsatisfactory. The procedure is highly unpredictable and errors in refraction exceeding thirty percent of the expected change are common. Decrease in the patient's best corrected visual acuity is also encountered following epikeratophakia. The refractive change achieved by epikeratophakia is not adjustable, and patients who are grossly over or under corrected must have the lenticule removed and replaced.

A second technique to correct refractive er4rors, termed photorefractive keratectomy, has recently been developed. Energy generated by a pulsed argon fluoride excimer laser at a wavelength of 193 nm causes a precise removal of corneal tissue without adjacent thermal or mechanical damage. Several optical laser delivery systems have been described which attempt to achieve a controlled etching of the anterior cornea to the desired refractive curvature. Unfortunately, three major shortcomings render this technique clinically unacceptable for some patients: scarring, unpredictable outcome, and refractive instability.

Since this procedure is performed directly in the visual axis, any scarring is unacceptable. Several investigators have demonstrated relatively dense opacification of the cornea in animals following photorefractive keratectomy with the 193 nm excimer laser. Although the scarring may be reduced by improvements in the optics of the delivery systems, there will remain very significant risks associated with irreversible treatment of the central optical axis of the eye.

A second problem with photorefractive keratectomy is the unpredictable refractive outcome of the technique. The final curvature of the ablated cornea will be influenced by stress and strain distribution changes occurring following ablation. Since the eye is a pressurized sphere, removal of some of its anterior surface causes the remaining tissue to accept a higher load of wall tension caused by the intraocular pressure. The net affect of this redistribution will cause the ablated cornea to shift in an anterior direction following photorefractive keratectomy, inducing a steepening of the optical zone. The extent of this shaft will vary with the intraocular pressure, the patient's age, and tissue characteristics and therefore can cause significant variations in optical outcome.

Another serious problem with direclty reprofiling the central area of the anterior corneal surface is the inability of the procedure to achieve a stable outcome. The majority of the thickness of the cornea is termed with stroma and consists of water, collagen fibers, a matrix substance, and numerous cells called keratocytes. The keratocytes, which reside between Bowman's layer and Descemet's membrane, help produce and maintain the collagen structure of the corneal stroma. These cells are also responsible for wound healing following corneal injury. When Bowman's layer is violated, these cells produce new collagen as scar tissue and attempt to reform the injured or disrupted fibers. The cornea heals in a very slow fashion with the keratocytes laying down and remodeling new collagen over many months to years.

During photorefractive keratectomy, a certain depth of the anterior cornea is ablated, depending on the refractive change desired. The more refractive change needed, the deeper the required ablation. Despite the fact that the collagenous surface re-epithelializes normally after laser ablation, the keratocytes begin to produce new collagen in an attempt to restore the thinned stroma. This regeneration of new collagen (which is highly variable) in the anterior stroma will cause the corneal curvature to continually change as new collagen is added.

In addition to stroma collagent regeneration, investigators have noted a compensatory thickening of the epithelium following photoablative keratectomy. This hyperplastic epithelium, which may result from wound healing mediators, will vary in its thickness over time and contribute to the instability or the refractive outcome. Since the processes of stromal collagen regeneration and epithelial hyperplasia occur over a long period of time, the refractive power of the eye will be constantly fluctuating for many months or years following the procedure.

SUMMARY OF THE INVENTION

It is, therefore, one of the principal objects of the present invention to provide an apparatus and process for application of a synthetic lenticule for effecting corrections in visual acuity obviating the need for glasses and/or contact lenses, the process including steps for safely and easily reprofiling the lenticule after application without its removal should future corrections be necessary.

Another object of the present invention is to provide a process for application of a synthetic lenticule which does not require ablation of the central corneal region or Bowman's layer, thereby avoiding disturbance of the visual axis of the patient.

A further object of the present invention is to provide an apparatus and a process in which the synthetic lenticule can be safely and easily removed and replaced with a different synthetic lenticule if necessitated by the physical condition of the patient or by other factors.

A still further object of the present invention is to provide a process which corrects refractive errors in patients and which avoids the previously mentioned problems associated with current techniques and procedures.

These and additional objects are attained by the present invention which relates to an apparatus and a process for application and reprofiling, if necessary, a synthetic lenticule for vision correction. The process first involves the removal of the overlying epithelium. A synthetic lenticule, which has been formed to correct the parricular refractive error in the patient's vision, is then secured over the undisturbed central corneal region utilizing the present apparatus. The application of the lenticule may be carried out under vacuum conditions and certain pharmacological agents may then be applied to the surface of the lenticule to enhance the regrowth of the normal epithelial cells over the lenticule. A further step includes selective reprofiling of the lenticule by laser ablation for refining the refractive power of the lenticule.

The process thus provides a safe and effective means for correcting visual acuity without the central surgical invasion of the cornea attendant in certain prior art techniques. Adjustment or fine tuning of the visual correction imparted is quickly and easily performed in a matter of minutes if needed after application of the lenticule.

Various additional objects and advantages of the present invention will become apparent from the following description, with reference to the accompanying drawings.

BRIEF DESCRIPTION OF THE DRAWINGS

FIG. 1 is a partial, side elevational and cross-sectional view of the outer half of a normal eye.

FIG. 2 is an enlarged; partial cross-sectional view of the outer half of the eye, shown prior to the operation embodying the present process;

FIG. 3 is an enlarged, partial cross-sectional view, similar to the preceding figure, with the epithelium removed, exposing the anterior surface layer of the cornea;

FIG. 4 is an enlarged, partial cross-sectional view, similar to the preceding figure, shown with the outer peripheral groove formed in the cornea;

FIG. 10 is an enlarged, partial, cross-sectional view, similar to the preceding figure, schematically illustrating reprofiling of the lenticule;

DETAILED DESCRIPTION OF THE PREFERRED EMBODIMENT

Figure 5:
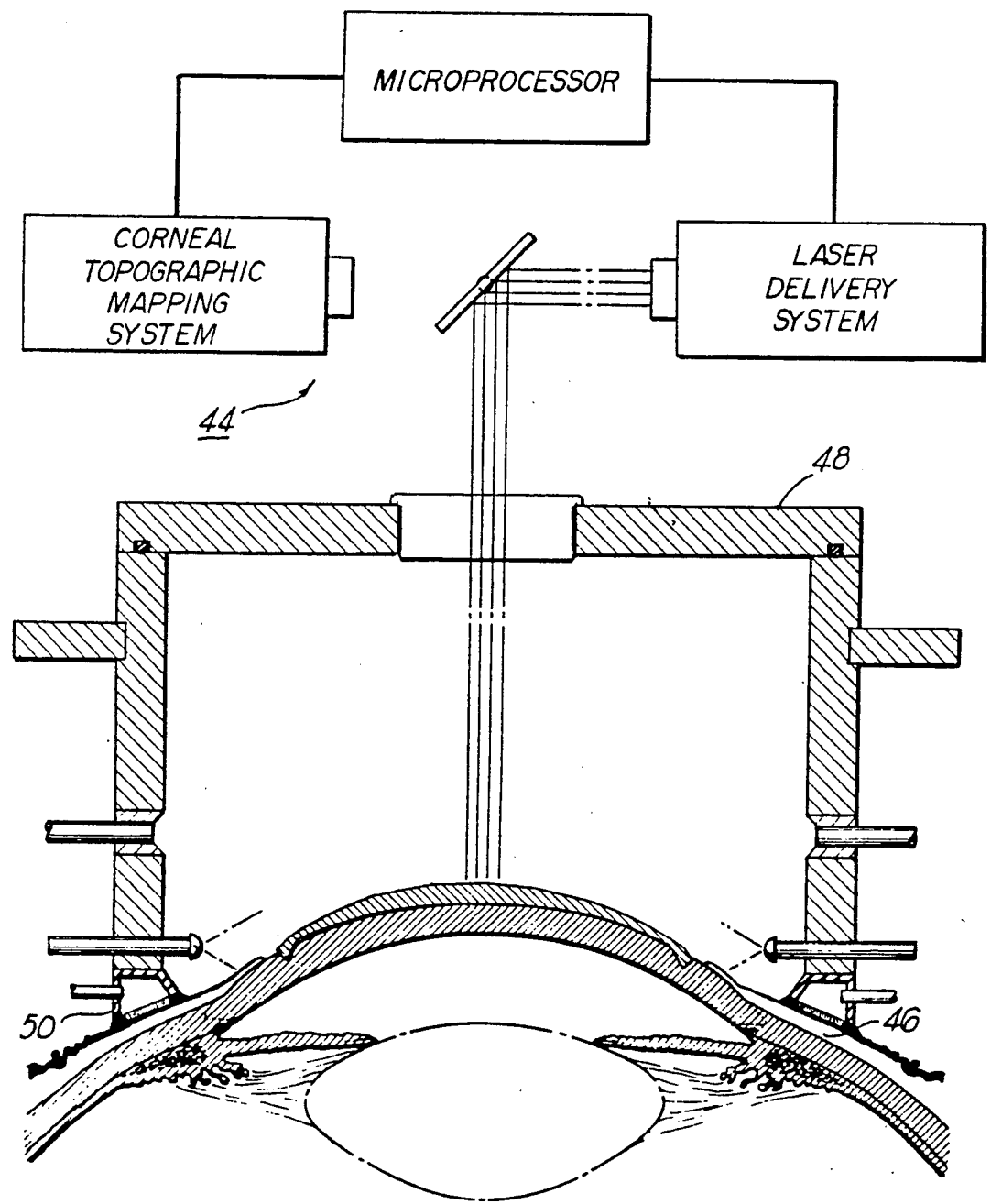
FIG. 5 is a diagrammatical view of a laser apparatus suitable for ablating the peripheral groove or slit and for reprofiling the lenticule.

Referring now more specifically to the drawings, and to FIG. 1 in particular, numeral 20 designates generally the outer half of the human eye upon which the present process for vision correction is performed, portions thereof being dsecribed hereinbelow as an aid in understanding the present process. The portions of the cornea 21 of the eye which are involved in the present process include an otuer layer of epithelial cells 22 which cover the outer cornea, which is known as Bowman's layer 24. The cornea has an inner corneal membrane 26, known as Descemet's membrane, which has a covering layer 28 on its posterior surface, termed the endothelium. Between the anterior and posterior boundaries are layers of striated tissue, termed the stroma 30, which comprise the bulk of the cornea 21.

The visual axis of the eye, one point of which is indicated generally at 32, can be considered as an imaginary line which extends through the central region, including the cornea 21, the lens 34, and the vitrieous region 36 to the rear of the eyeball near the optic nerve (not shown). Theis central region of the cornea is the most important region of the cornea with regard to the vision of the patient. This factor, which has been observed in the outcomes of several of the prior art techniques previously described, is a major reason why the present process specifically avoids any surgical invasion of the central region of the cornea.

FIG. 2 illustrates in magnified detail the section of the eye shown in FIG. 1, shown prior to beginning the process embodying the present invention. Before any corrective measures are undertaken, a detailed analytical profile of the patient's cornea is made and analyzed by the physician. Such a profile may be obtained from a corneal topographic mapping system such as, for example, the Corneal Modeling System developed by the Computer Anatomy Corp. of New York, N.Y. Such computer modeling provides the physician with a three dimensional profile of the cornea and precisely defines its anterior shape. Thus, patients with refractive errors would undergo ocular examinations to obtain data used in determining the lenticule manufacturing criteria. Corneal topographic data is used to determine the posterior shape of the lenticule, and refractive data is used to determine the anterior shape. The lenticule can then be manufactured to meet individual patient specifications.

Armed with this data, the physician designs and orders an appropriate lenticule having the desired refractive characteristics. The lenticule is manufactured from a synthetic or reconstituted polymer, such as a preferred synthetic collagenous polymer, or other suitable synthetic material that is biocompatible with the tissues of the eye. The lenticule is prepared and treated with appropriate chemical means to achieve the desired properties of constituency, optical clarity and stability. The material also has characteristics such that is is resistant to invasion and/or degradation by cells and cellular agents. The material can be shaped to the desired specifications by injection molding, lathe cutting, laser profiling, or a combination of these and/or other techniques. Additionally, the material used for the lenticule has the capability to support and maintain epithelial growth in a normal fashion over its anteriro surface and has favorable optical characteristics for the transmission of light in the visible spectrum. A final requirement of the synthetic material is that it will allow laser reprofiling of its anterior surface after attachment to the cornea, which is a significant and unique step disclosed by the present inventive process. Such materials meeting the above requirements are currently available on the market and other suitable synthetic materials are likely to be developed. It is important to note however, that the present process does not involve or contemplate the use of donor corneal material from a human eye.

With the detailed profile of the anterior surface of the cornea, that is, Bowman's layer 24, provided by a suitable mapping system, the posterior surface 38 of the lenticule 40 (FIG. 8) is configured such that is precisely matches the patient's anterior corneal curvature after the removal of the epithelium 22. The anterior surface 42 of the lenticule, which serves as the new optical curve for the cornea, is profiled prior to application to the curvature necessary to correct the patient's refractive error. This determination is derived from a database which includes, but is not limited to, factors such as the axial length of the eye, manifest refraction, cycloplegic refraction, manual retinoscopy, automated retinoscopy, and automated refraction. Allowance is also made for the thickness of the pithelium which will recover the lenticule.

With the synthetic lenticule prepared, reference is made to FIGS. 3 through 11, which illustrate the additional steps of the present invention. The corneal epithelium 22 is normally removed mechanically, as shown in FIG. 3, with a chemical solution on a swab or by other suitable means.

FIG. 5 illustrates diagrammatically a combination scanning device for mapping the contour of the eye and laser delivery system 44, a preferred system providing energy generated by a pulsed laser for reprofiling the lenticule after its application. One suitable laser system is an argon fluoride exicmer laser, the energy produced having a wavelength of 193 nm. The system is capable of a precisely determined removal of material, such as formation of a groove or excision, without thermal or mechanical damage to adjacent regions. Such a system is discussed in U.S. Pat. No. 4,665,913 to L'Esperance, Jr. for a Method For Epthalmological Surgery. Other suitable laser delivery systems may also be used, such as a 2.9 micron infrared laser system.

Figure 6:
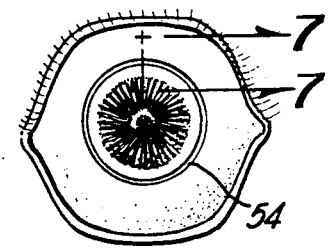

The patient's eye is fixed at the limbus 46, to the housing 48 of the system, by a limbal suction ring 50, a vacuum within the ring being created by evacuating the air within the ring through ports 51. Taking into consideration the diameter and the configuration of the peripheral edge 52 of the prepared lenticule 40, the laser delivery system is programmed to etch a shallow peripheral groove 54, extending into or through Bowman's layer 24 and into the stroma 30. A template (not shown) or a specialized lens, such as an axicon lens (not shown) may be used to direct and focus the microprocessor controlled laser output, forming the groove in a peripheral, optically insignificant region of the cornea. THus, as shown in FIG. 6, the groove is formed well outside the visual axis of the patient. In addition to a suitable laser delivery system, mechanical cutting means, such as a trephine, may be used to form the groove provided the mechanical means used includes the required precision to form the groove without damage to adjacent tissue under the control of a skilled surgeon.

Figure 7:
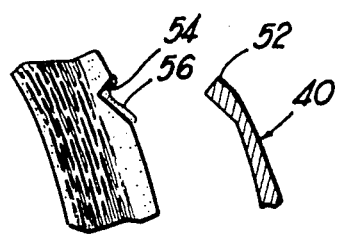
FIG. 7 is an enlarged, partial, cross-sectional view showing a sealant means disposed in the groove for receiving the edge of the lenticule, the view being taken on line 6—6 of FIG. 5.

With the groove 54 formed, a suitable adhesive maens 56 is applied therein to receive and bond the lenticule to the cornea, as shown in FIG. 7. A preferred adhesive is a collagen-based glue so as to be biocompatible with the corneal stroma and with the lenticule. Other suitable securing means may also be used, for example, suturing, with a suitably prepared lenticule, preferably having preformed apertures to receive the sutures, thus preventing asymmetrical tension on the eye or lenticule.

Figure 8:
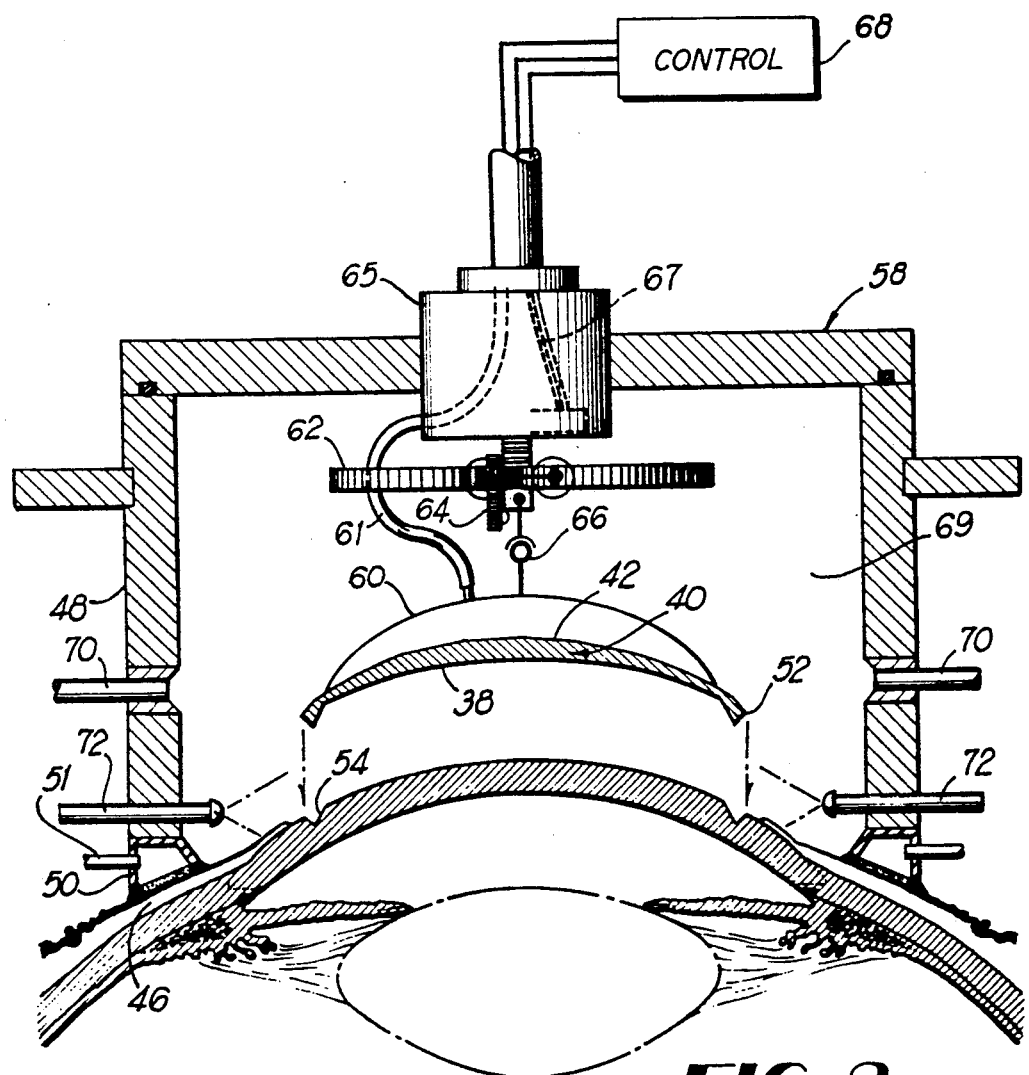
FIG. 8 is a diagrammatical view, shown partially in cross-section, of the apparatus used for placing the lenticule over the cornea.

FIG. 8 diagrammatically illustrates the lenticule application apparatus 58. The eye is fixed as shown in FIG. 5, like elements being defined by like numerals, with suction ring 50 securing the apparatus to the limbus 46 of the eye. The apparatus is similar in use to that shown in FIG. 5 as far as attachment to the eye; however, certain features have been added as described hereinbelow. The lenticule 40 is held by a suction ring 60 having a vacuum line 61, the ring 60 being attached to a micromanipulator system. The vacuum line communicates with the posterior surface of the suction ring to as to selectively create a vacuum between the ring and the lenticule. The micromanipulator has a horizontal carriage 62, a vertical carriage 64, and a 360° gimbal 66, thus being capable of movement in any axis as well as translations across these axes. The unit is powered through electrical power lines or cables 67 and is driven by a motor 65 which receives signals from a microprocessor 68. The micromanipulator unit is controlled by the surgeon with conventional remote control means (not shown). After the adhesive means 56 is applied in the groove by a suitable application (not shown), the main chamber 69 is evacuated of air through suction ports 70. With a sufficient vacuum obtained, the lenticule 40 is lowered into position on the cornea. The surgeon may utilize fiberoptic viewing ports 72 to assist in alignment of the peripheral edge 52 of the lenticule with the groove 54.

Figure 9:
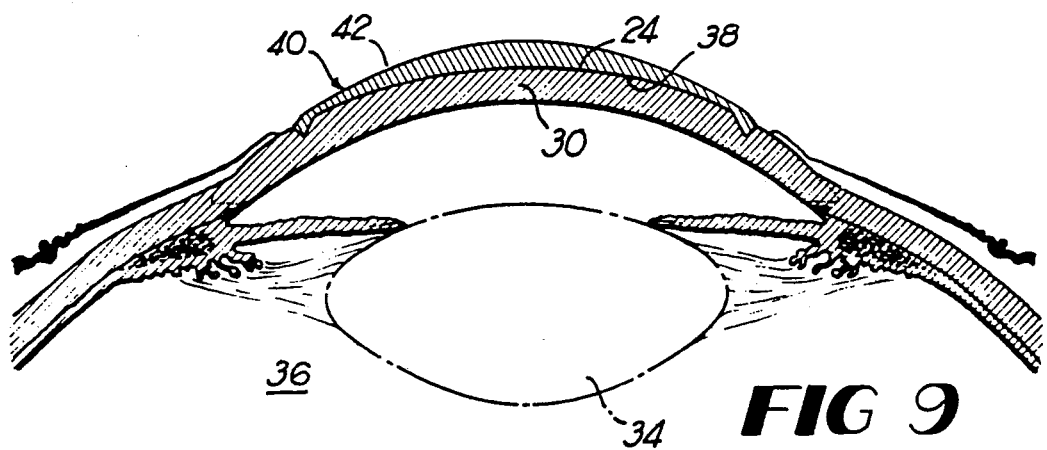
FIG. 9 is an enlarged partial, cross-sectional view, similar to FIG. 4, showing the lenticule secured in place over the cornea.
Figure 10:
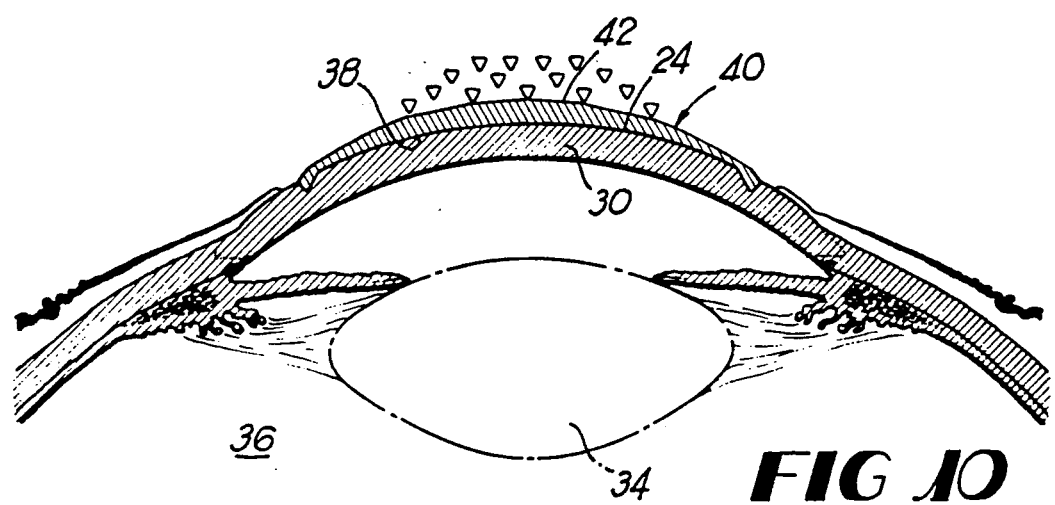
FIG. 10 is a partial top plan view of the eye, corresponding to the view shown in FIG. 4.

Once the lenticule is in position, as shown in FIG. 9, the vacuum in the main chamber is released. Since the mating of the lenticule with the corneal surface occurs under conditions of low pressure, the return of ambient air pressure causes a firm seating of the lenticule to the cornea. This assures good approximation of the posterior surface of the lenticule to the corneal layer during the bonding period of the glue which normally takes several minutes. The glue achieves permanent bondong of the peripheral edges of the lenticule in the groove. The precision etching of the groove by the laser, as dictated by the diameter of the lenticule and the configuration of the peripheral edge 52 thereof, assures that the anterior surface of the edge portion is substantially flush with the outer, adjacent corneal layer, thus providing no mechanical barrier to the pithelial cell layer which then regrows over the lenticule.

Immediately after attachment of the lenticule, the anterior curvatures can be remeasured to determine if the anticipated correction has been achieved. If there were inaccuracies in the initial calculation of the lenticule, or changes in lenticule curvature due to the attachment technique, these may be immediately corrected by laser reprofiling of the lenticule by the laser delivery system.

After placement of the overlay into position on the cornea, certain pharmacological agents may be applied which enhance and speed the growth of epithelial cells over the lenticule, agents such as fibronectin, epidermal growth factor, and antibiotics. With these agents, epithelial covering will normally be complete within several days, this being illustrated in FIG. 11.

After the lenticule is covered with epithelium, it is expected the patient's refractive error will be largely, if not completely, corrected. However, if further refractive adjustments are necessary, a suitable laser delivery system, as previously described and shown in FIG. 5, can be used to reprofile the anterior curvature of the lenticule to the desired shape. The data used to determine reprofiling criteria are determined in follow-up examinations and may include the previous data obtained on the patient, corneal topographic mapping, automated and cycloplegic refraction measurements, and any other pertinent data.

Figure 11:
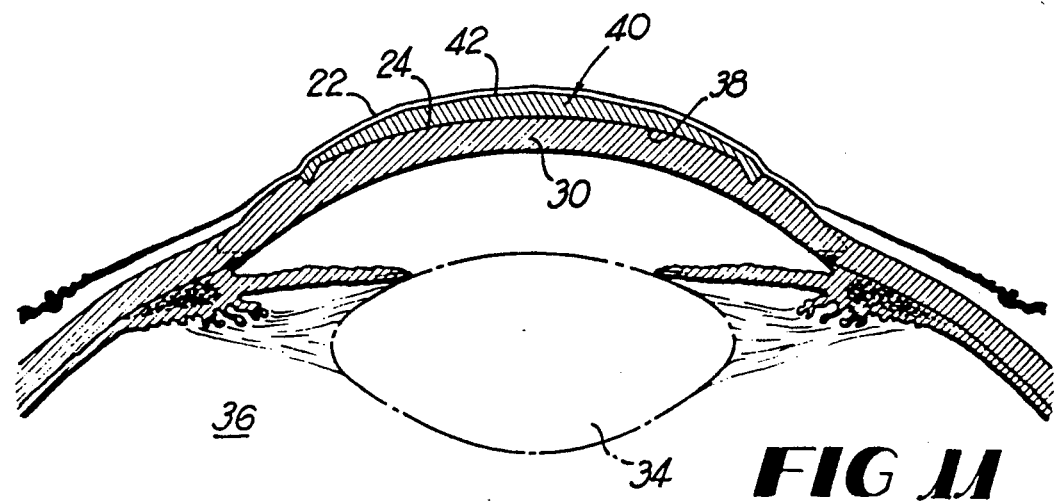
FIG. 11 is an enlarged, partial cross-sectional view, similar to the preceding figure, showing the reprofiled lenticule in place with the epithelium regrown thereover.

Should reprofiling of the lenticule be required ata ny time after placement of the overlay, the corneal epithelium is removed as previously described, the eye then being as shown in FIG. 9. The laser delivery system shown in FIG. 5 is set up and the eye is fixed at the limbus 46 as discussed hereinabove. Assuming, for example, that a myopic condition still exists or develops later, the laser is directed to reprofile the surface of the lenticule 40 in the central region thereof, thereby reducing the curvature, this being schematically illustrated in FIG. 10. To increase the curvature, the laser ablation would be directed to the peripheral regions of the lenticule (not shown), thus steepening the curve and adjusting for a hyperopic condition. After reprofiling, the epithelium regrows over the lenticule, as shown in FIG. 11. Thus, the lenticule's design, including its thickness and composition, allows for laser reprofiling of its anterior surface after attachment to the patient's eye. Such reprofiling allows correction of residual refractive errors. The process thus provides patients with refractive errors an alternative means of correcting their vision without the need for spectacles, contact lenses, or current surgical techniques, and allows for future corrections to be made as needed.

Thus, it is believed apparent to those skilled in the art, the many advantages of the process of applying a synthetic overlay, laser-adjustable, refractive surface over present techniques of refractive surgery including improved safety, predictability, and stability, as well as the option to adjust or remove the overlay.

The safety of the process is evident in that the central optical zone of the patient'socrnea is never violated. A shallow peripheral exicsion is made well outside of the visual axis. In contrast, photorefractive keratectomy involves directly ablating corneal tissue within the optical zone. Any malfunction of the laser delivery system, debris on the cornea, or unintended ocular motion during ablation will result in severe optical effects for the patient.

Compared with current techniques, no significant structural weakening of the cornea occurs with the method described with this invention. Radial keratotomy, on the other hand, significantly weakens the cornea by making multiple, near full thickness incisions. Photorefractive keratectomy will remove a variable amount of anterior corneal tissue depending on the required refractive change. For example, correcting a 10 dipter refractive error over a six mm optical zone will require removign nearly 20% of the corneal thickness, a very significant amount.

Another safety advantage to the synthetic overlay technique is the avoidance of direct irradiation of the optical axis of the eye with far ultraviolet laser energy. Although current eivdence suggests the 193 nm exicmer lasers appears to be safe for corneal surgery, long term hazards such as delayed corneal scarring are minimized by confining laser ablation to a small peripheral region of the cornea which is optically insignificant to the patient.

A significant improvement in predictability in refractive outcome is provided by the present technique. Since there is no significant structural weakening of the cornea, variables induced by curvature changes of the patient's cornea will not be encountered after the procedure, the actual result closely approximating, if not matching, the anticipated change.

Once the lenticule covers with epithelium, the refractive result remains stable over time. Since the overlay is composed of a material which prevents invasion or degradation by cells or cellular agents, no refractive shift caused by collagen deposition or removal is encountered as is seen in photorefractive keratectomy.

A further, significantly unique feature of the synthetic overlay process described herein is the abiliyt to adjust the refractive power of the lenticule after it is placed on the cornea. Unlike procedures such as radial keratotomy or epikeratophakia which are not adjustable, the overlay can be reprofiled while in place on the corneal surface if a new refractive power is needed. Although photorefractive keratectomy procedures could be repeated on patients who did not achieve their desired correction, each treatment would irreversibly remove more of the patient's central corneal tissue, and risk causing corneal scarring with treatment.

The techniques described in this invention provide a mechanism to apply and secure a synthetic lenticule to the surface of the eye while avoiding the undesirable mechanical distorting forces associated with present techniques of corneal bed preparation and suturing. Achieving a precise fit of the lenticule to the host bed with a tolerance of only a few microns is highly important. Corneal trephination evices or mechanical cutting instruments may be used to form a peripheral incision or slit in the cornea for receiving the edge of the lenticule. In addition, grooving the cornea with the delivery optics described in this invention for the embodiment of FIGS. 1 through 11 represents a significant advancement in preparing the cornea for the lenticule.

Figure 12:
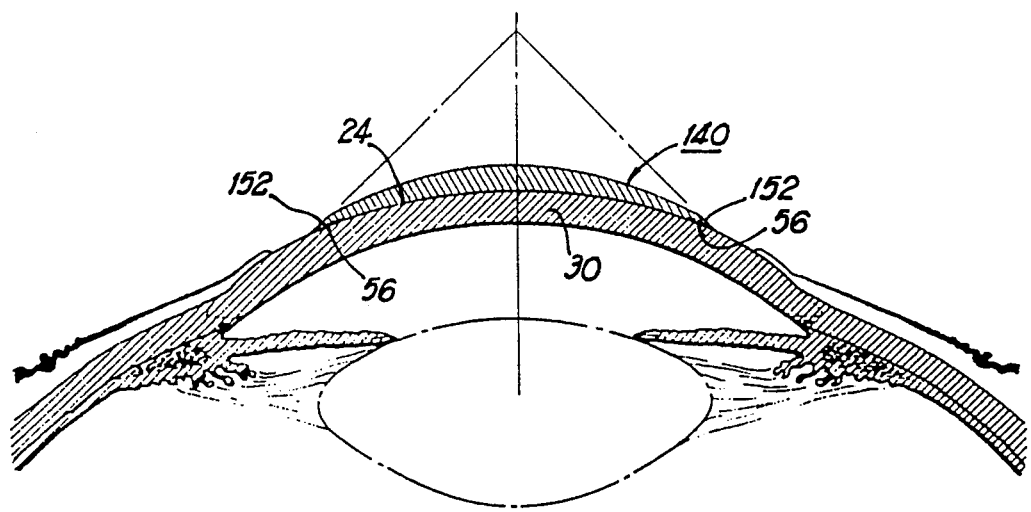
FIG. 12 is an enlarged, partial, cross-sectional view illustrating an alternate embodiment of the present invention in which no host bed preparation is done to the cornea.

Referring now to FIG. 12, an alternate embodiment of the present invention, with regard to the application of the lenticule, is illustrated in cross-section. In this embodiment, after the epithelium is removed, the lenticule 140 is applied directly over Bowman's layer 24 with no disturbance at all to Bowman's layer or the stroma 30. The peripheral edge 152 of the lenitcule is chamfered so as to provide a smooth transition between the lenticule edge and Bowman's layer, thus presenting no obstacle to the regrowth of the pithelial cell layer. The lenticule is secured in place with a suitable biocompatible adhesive means 56, which is applied either beneath the peripheral edge 152, as shown in FIG. 12, or where the adhesive is substantially completely transparent, beneath the entire lenticule, as shown in FIG. 13 for the succeeding embodiment, or by other suitable means.

This embodiment offers advantages in that no receiving means, i.e. a peripheral groove, slit, etc. is formed in the cornea, thus making the procedure completely reversible. Further advantages are identical to those discussed previously, regarding, among others; the amenability of the lenticule to profiling or reprofiling, using a suitable laser delivery system; the adjustability of the imparted vision correction; and the avoidance of any surgical invasion of the central corneal region, thus obviating the possibility of scarring from keratocyte regeneration or other factors.

Figure 13:
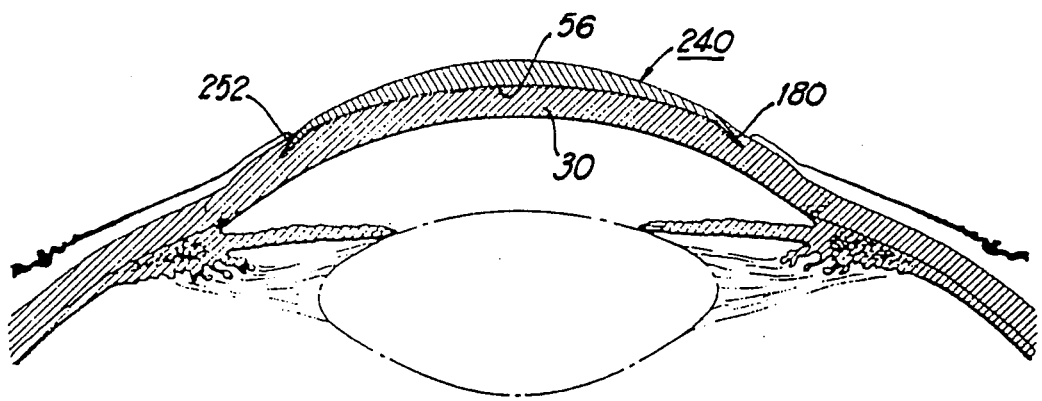
FIG. 13 is an enlarged, partial, cross-sectional view illustrating another embodiment inw hich a peripheral slit is formed in the cornea to receive the lenticule.
Figure 14:
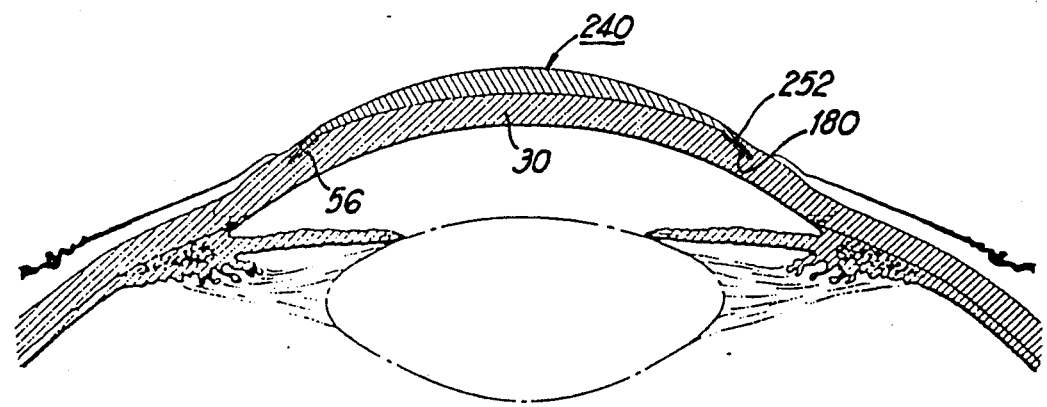
FIG. 14 is an enlarged, partial, cross-sectional view illustrating an alternate embodiment of the embodiment shown in the preceding figure.

FIGS. 13 and 14 illustrate another embodiment of the present invention, the application differing only in the use and placement of the securing means, as between the two figures. In each of the illustrated applications, a peripheral incision or slit 180 is formed in an optically insignificant region of the cornea, the slit being formed by any of a number of conventional means, such as a trephine. The chamfered edge 252 of lenticule 240 is inserted into the slit 180 where it is retained by means of the design of the chamfered edge portion and the angle at which the slit 180 is formed. The lenticule 240 may also be further secured by the application of an adhesive means 56 either beneath the entire lenticule, as shown in FIG. 13, or at the peripheral edge, as shown in FIG. 14.

In either case, lenticule 240 is designed with the same principles in mind as the previously described embodiments, providing the capability of profiling or reprofiling the lenticule with the laser after its application over the cornea, providing for reversibility of the operation with no disturbance of the central corneal region, and providing a smooth transition between the peripheral edge theeof and Bowman's layer, thus facilitating the regrowth of the epithelial layer.

Regardless of the skill of the surgeon, suturing will always impart asymmetric tension between the host cornea and lenticule. The method of attachment of the lenticule as described in this invention, including the use of collagen compatible adhesive and a vacuum system to create high surface tension between the cornea and the lenticule, represents a significant advance over presently available methods.

Finally, the method described herein is reversible. Unlike radial keratotomy or photorefractive keratectomy which are essentially iireversible procedures, the synthetic lenticule may be removed if unforeseen problems develop. Thus, a malfunction in the laser reprofiling delivery system when used as described above may render the synthetic lenticule optically unacceptable, but would leave the patient's central cornea completely intact, and a substitute lenticule can easily be applied.

While an embodiment of an apparatus and process for application and adjustable reprofiling of synthetic lenticules for vision correction and modifications thereof have been shown and described in detail therein, various additional modifications may be made without departing from the scope of the present invention.

I claim:

1. A process for application and adjustable reprofiling of a synthetic lenticule to the cornea of the human eye for correcting vision, comprising the steps of:
   (a) preparing a topographic map of the anterior surface of the cornea;
   (b) profiling the posterior surface of a synthetic lenticule to closely match the anterior surface of the cornea, said lenticule being constructed so as to correct the patient's particular refractive error and said lenticule being designed with the capability of being profiled through laser ablation;
   (c) removing the outer epithelial cell layer form the anterior surface of the cornea;
   (d) forming a shallow peripheral slit in the cornea, outside the visual axis of the eye;
   (e) applying adhesive means in said slit;
   (f) placing the peripheral edge of said lenticule in said slit whereby said lenticule is disposed over the cornea; and
   (g) ablating by laser predetermined portions of said lenticule for refining its refractive power.

2. A process as defined in claim 1 and including the additional step of applying pharmacological agents over said applied lenticule for enhancing epithelial growth thereover.

3. A process as defined in claim 2 and including the additional step of removing the regrown corneal epithelial layer and reprofiling said lenticule with a lser for further refining the refractive power of the lenticule.

4. A process as defined in claim 3 and including the additional step of applying pharmacological agents over said reprofiled lenticule for enhancing epithelial growth thereover.

5. A process as defined in claim 1 and including the additional step of creating a vacuum between said lenticule adn the cornea, prior to the application of said lenticule as defined in said step (f) for creating a negative pressure therebetween and facilitating seating of said lenticule on the cornea.

6. A process as defined in claim 1 wherein said slit is formed by a laser.

7. A process as defined in claim 1 wherein said slit is formed by a mechanical cutting means.

8. A process for application of a synthetic lenticule over the cornea of the human eye for correcting vision, comprising the steps of:
   (a) removing the outer epithelial cell layer from the anterior corneal surface layer;
   (b) profiling the posterior surface of a synthetic lenticule to closely amtch said anterior surface of the cornea, said lenticule being composed of a synthetic material with the inherent capability of being reprofiled after application over the cornea and also being constructed so as to correct the patient's particular refractive error;

(c) forming a shallow, peripheral slit in the exposed cornea, outside of the visual axis of the eye;

(d) securing the prepared lenticule over the cornea, disposing the peripheral edge thereof in said slit where it is fastened by a suitable securing means.

9. A process as defined in claim 8 and including the additional step of selectively ablating by laser predetermined portions of said lenticule for refining the refractive power thereof.

10. A process as defined in claim 8 in which said securing means includes an adhesive.

11. A process as defined in claim 8 in which said slit of step (c) is formed with a trephine.

12. A process as defined in claim 8 and including the additional steps of preparing a topographical map of the anterior surface of the cornea and profiling the posterior surface of said lenticule to closely approximate said anterior surface of the cornea.

13. A process as defined in claim 8 and including the additional step of applying pharmacological agents over said lenticule for enhancing epithelial growth thereover.

14. A process as defined in claim 8 and including the additional step of performing said step (d) under vacuum conditions.

15. A process for application and adjustable reprofiling of a synthetic lenticule to the cornea of the human eye for correcting vision said lenticule being formed from a synthetic material that is resistant to degradation from cells and cellular agents, comprising the steps of:

(a) removing the outer epithelial cell layer from the anterior corneal surface layer;

(b) profiling the posterior surface of a synthetic lenticule to closely amtch said anterior surface of the cornea, said lenticule being composed of a synthetic material with the inherent capability of being reprofiled after application over the cornea and also being constructed so as to correct the patient's particular refractive error;

(c) ablating by laser a receiving means for said lenticule in the exposed cornea, outside of the visual axis of the eye;

(d) applying an adhesive means in said receiving means; and (e) placing the prepared lenticule over the cornea, disposing the peripheral edge thereof in said receiving means where it is secured by said adhesive means.

16. A process as defined in claim 15 and including the additional step of selectively ablating by laser predetermined portions of said lenticule for refining the refractive power thereof.

17. A process for application and adjustable reprofiling of a synthetic lenticule to the cornea of the human eye for correcting vision, comprising the steps of:

(a) preparing a topographic map of the anterior surface of the cornea;

(b) profiling the posterior surface of a synthetic lenticule to closely match the atnerior surface of the cornea, said lenticule being constructed so as to correct the patient's particular refractive error and being designed with the capability of being reprofiled after the application thereof over the cornea;

(c) removing the outer epithelial cell layer from the anterior surface of the cornea;

(d) applying an adhesive means to the cornea, outside the visual axis of the eye, for receiving the peripheral edge of said lenticule;

(e) placing said lenticule over the cornea, the peripheral edge theerof being received by said adhesive means, said lenticule thus being disposed over the cornea; and (f) ablating by laser predetermined portions of said lenticule for refining its refractive power.

18. The process as defined in claim 17 in which said adhesive means is applied to the cornea so as to receive substantially the entire posterior surface of said lenticule.

19. A process for application and adjustable reprofiling of a synthetic lenticule to the cornea of the human eye for correcting vision, comprising the steps of:

(a) removing the outer epithelial cell layer from the anterior corneal surface layer;

(b) forming a shallow, peripheral slit in the exposed cornea, outside of the visual axis of the eye;

(c) maneuvering said lenticule into position over the cornea and creating a vacuum between said lenticule and the cornea for creating a negative pressure therebetween;

(d) securing the prepared lenticule over the cornea, disposing the peripheral edge thereof in said slit where it is fastened by a suitable securing means; and (e) releasing said vacuum, the return of the ambient air pressure facilitating the seating of said lenticule on the cornea.

20. The process as defined in claim 19 inw hich said securing means is applied to the cornea for receiving said lenticule.

21. A process for application and adjustable reprofiling of a synthetic lenticule to the cornea of the human eye for correcting vision, comprising the steps of:

(a) preparing a topographic map of the anterior surface of the cornea;

(b) profiling the posterior surface of a synthetic lenticule to closely match the anterior surface of the cornea, said lenticule being constructed so as to correct the patient's particular refractive error and being designed with the capability of being reprofiled after the application thereof over the cornea;

(c) removing the outer epithelial cell layer from the anterior surface of the cornea;

(d) applying an adhesive means to the cornea, (e) placing said lenticule over the cornea, for being received by said adhesive means, said lenticule thus being disposed over the cornea; and (f) ablating by laser predetermined portions of said lenticule for refining its refractive power.

22. A process for application and adjustable reprofiling of a synthetic lenticule to the cornea of the human eye for correcting vision, comprising the steps of:

(a) profiling the posterior surface of a synthetic lenticule to closely match the anterior surface of the cornea, said lenticule being constructed so as to correct the patient's particular refractive error and being designed with the capability of being reprofiled after the application thereof over the cornea;

(b) removing the outer epithelial cell layer from the anterior surface of the cornea;

(c) applying an adhesive means to said lenticule;

(d) placing said lenticule over the cornea, for being adhered thereto; and (e) ablating predetermined portions of said lenticule for refining its refractive power.

23. A process for application of a synthetic lenticule over the cornea of the human eye for correcting vision, said lenticule being constructed so as to closely match the anterior surface of thecornea and to correct the patient's particular refractive error, and said lenticule being composed of a synthetic material with the inherent capability of being ablated to adjust the anterior surface thereof, said process comprising the steps of:

(a) removing the otuer epithelial cell layer from the anterior surface of the cornea;

(b) securing said lenticule to said anterior surface of the cornea; and (c) ablating the anterior surface of said lenticule for refining the correction factor imparted by said lenticule.

24. A process for application and ablation of a synthetic lenticule over the cornea of the human eye for correcting vision, said lenticule being constructed such that the posterior surface thereof closely matches the anterior surface of the cornea, said process comprising the steps of:

(a) removing teh outer epithelial cell layer form the anterior surface of the cornea;

(b) securing said lenticule to said anterior surface of the cornea, said lenticule being composed of a synthetic material having the inherent capability of being ablated and being constructed so as to correct the patient's particular refractive error; and (c) ablating the anterior surface of said lenticule to the extent necessary to obtain the required vision correction.

25. A process for application and adjustable profiling of a synthetic lenticule to the cornea of the human eye for correcting vision, comprising the steps of:

(a) removing the epithelial layer from the anterior surface of the cornea; and (b) securing the lenticule in place over the cornea, said lenticule having the inherent capability to be laser profiled and being resistant to invasion by cells and cellular agents.

26. A process for application of a synthetic lenticule over the cornea of a human eye for correcting vision, comprising the steps of:

(a) determining the correction needed by the patient;

(b) shaping said synthetic lenticule to impart the desired correction of vision;

(c) removing the epithelial layer from the anterior surface of the cornea; and (d) securing said lenticule over the cornea, said lenticule being resistant to invasion by cells and cellular agents.

27. A process for application of a synthetic lenticule over the cornea of a human eye for correcting vision, comprising the steps of:

(a) determining the correction needed by the patient;

(b) removing the epithelial layer from the anterior surface of the cornea;

(c) securing said lenticule over the cornea, said lenticule being resistant to invasion by cells and cellular agents; and (d) profiling said synthetic lenticule to a shape that corrects the vision of the patient.

28. A process for application of a synthetic lenticule over the cornea of a human eye for correcting vision, comprising the steps of:

(a) determining the correction needed by the patient;

(b) removing the epithelial layer from the anterior surface of the cornea;

(c) profiling said synthetic lenticule to a shape that corrects the vision of the patient; and (d) securing said lenticule over the cornea, said lenticule being resistant to invasion by cells and cellular agents.

* * * * *